United States Patent [19]

Pohl et al.

[11] Patent Number: 5,578,060
[45] Date of Patent: Nov. 26, 1996

[54] PHYSICAL THERAPY APPARATUS HAVING AN INTERACTIVE INTERFACE, AND METHOD OF CONFIGURING SAME

[75] Inventors: Jeff K. Pohl, Chattanooga; David A. Johnson, Signal Mountain; Edward R. Dunlay, Harrison, all of Tenn.

[73] Assignee: Chattanooga Group, Inc., Hixson, Tenn.

[21] Appl. No.: 494,095

[22] Filed: Jun. 23, 1995

[51] Int. Cl.$^6$ .............................. A61N 1/08; A61H 1/00
[52] U.S. Cl. .................................. 607/3; 601/2; 601/15; 607/46
[58] Field of Search .................................. 607/1, 2, 3, 87, 607/46, 48, 59, 98, 62; 601/2, 15; 128/660.01, 660.03; 364/413.27, 413.01, 413.02

[56] References Cited

U.S. PATENT DOCUMENTS

| | | | |
|---|---|---|---|
| 3,735,756 | 5/1973 | Richards et al. | 607/3 |
| 4,580,570 | 4/1986 | Sarrell et al. | |
| 4,690,146 | 9/1987 | Alon | |
| 5,041,974 | 8/1991 | Walker et al. | 364/413.27 |
| 5,054,774 | 10/1991 | Belsito | |
| 5,088,037 | 2/1992 | Battaglia | 364/413.01 |
| 5,255,187 | 10/1993 | Sorenson | 364/413.02 |
| 5,265,010 | 11/1993 | Evans-Paganelli et al. | 364/413.02 |
| 5,394,871 | 3/1995 | Sauer et al. | 128/660.01 |
| 5,403,251 | 4/1995 | Belsito et al. | |

OTHER PUBLICATIONS

Chattanooga Group, Inc. brochure, *Touch The New World Of Healing Technology, Forte™*, Form #2035, 1994.
Chattanooga Group, Inc., *Forte™ CB Operator's Manual*, P.N. 76788C, Nov. 1994.
Chattanooga Group, Inc., *Forte™ ES Service Manual*, P.N. 76911A, Nov. 1994.
Chattanooga Group, Inc. brochure, *Intelect® 900 Electrotherapy System*, Form #2032A, 1993.
Chattanooga Group, Inc. brochure, *Intelect® 170 Low Volt/Ultrasound Combo*, Form #2020, 1993.
Chattanooga Group, Inc., *Intelect™ 900 Operator's Manual*, P.N. 76502, Rev. A, Oct. 1992.
Chattanooga Group, Inc. brochure, *Intelect® 245 MP Ultrasound*, Form #2029, 1992.
Chattanooga Group, Inc. brochure, *Intelect® VMS™ II, Variable Muscle Stimulator*, Form #2023, 1990.

*Primary Examiner*—William E. Kamm
*Assistant Examiner*—George R. Evanisko

[57] ABSTRACT

A reconfigurable physical therapy apparatus and a method of providing operator-selected stimuli to a patient are provided. The apparatus preferably has a physical therapy applicator including a transducer for applying a therapeutic treatment to a patient, and a memory for storing identification data representative of a plurality of physical ailments for each of a plurality of human body areas and a set of transducer operational parameters associated with each predetermined physical ailment and each predetermined body area. The apparatus also has an ailment display screen responsive to the memory device for displaying at least one of the identification data representative of a plurality of physical ailments which are associated with at least one of the identified human body areas. An ailment selector is positioned in electrical communication with at least the memory device and being responsive to operator selection of one of the identified physical ailments which are associated with human body areas for obtaining the associated transducer operational parameters. The apparatus further has a transducer reconfigurer positioned in electrical communication with the transducer of the applicator and being responsive to the ailment selector for reconfiguring the transducer to provide therapeutic treatment to the identified body part according to the obtained transducer operational parameters.

37 Claims, 17 Drawing Sheets

Clinical Protocols

ELECTRICAL STIMULATION: PAIN MANAGEMENT (page 1 of 4)

| | Pain Management | Wave | Parameters | Rational |
|---|---|---|---|---|
| | CERVICAL STRAINS | | | |
| Select | Acute, well localized pain | IFC | 80-150 Hz Scan | Enkephalin release, gait theory, decrease accommodation. |
| Select | Subacute or generalized pain | IFC | 1-150 Hz 100% Scan | Combination of endorphin/enkephalin theories. |
| Select | Chronic pain | IFC | 5 Hz | Endorphin release |
| | CERVICAL STRAINS | | | |
| Select | Acute, well localized pain | Premod | 80-150 Hz | Enkephalin release, gait theory, decrease accommodation. |
| Select | Subacute or generalized pain | Premod | 1-150 Hz | Combination of endorphin/enkephalin theories. |
| Select | Chronic pain | Premod | 1-10 Hz | Endorphin release |
| | CERVICAL Brachial Plexus Injury | Premod | 80-150 Hz | Enkephalin release, gait theory, decrease accommodation. |

*FIG. 4B*

Clinical Protocols 

ELECTRICAL STIMULATION: MUSCLE CONTRACTION/STRENGTHENING (page 1 of 5)

| Physiological Need | Wave | Parameters | Rational |
|---|---|---|---|
| Reeducation (General) | VMS | 4/12 Re-ed | 1:3 ratio, short contraction for initial treatment |
| | VMS | 8/24 Pattern | 1:3 ratio, varied frequency to minimize fatigue |
| | VMS Burst | 10/20 Re-ed | 1:2 ratio for more aggressive rehab |
| | VMS Burst | 10/50 Re-ed | 1:5 ratio for initial treatments or full recovery between maximum contractions |
| | Premod | 10/30 3 Ch Recruit | Facilitate proper recruitment order for functional recovery. |
| | Premod | 10/30 Re-ed | 1:3 ratio for general applications |

Select Select Select Select Select Select

FIG. 4C

Clinical Protocols

| ELECTRICAL STIMULATION: WOUND MANAGEMENT (page 1 of 2) | | | |
|---|---|---|---|
| Pathology | Wave | Parameters | Rational |
| Stage III or IV Wounds | Monophasic | 128 pps, negative polarity at subsensory output (approx. 30 min). Treatment time 30 minutes, BIO. Treatments are 5-7 days per week. Negative polarity is used until the wound is debrided or a sero-sanguinous drainage appears, and the negative polarity is continued for 3 days longer. Polarity is then switched to positive, preset at 128 pps and continued for 3 days until ulcer heals to stage II. Then follow guidelines below. | Several studies have shown that low level direct or pulsed currents augment the healing of chronic wounds in humans and induced wounds in animals. Feedar, et al, studied stage II, III, or IV pressure ulcers, ulcers from vascular insufficiency, and wounds caused by trauma or surgery. Guidelines developed by a multi-disciplinary panel and the U.S. Dept. of Health and Human Services recommend electrical stimulation for stage III and IV pressure ulcers that are unresponsive to conventional therapy or recalcitrant stage II ulcers. |
| Stage II Wounds | Monophasic | Begin treatment with Preset at 64 pps, negative polarity, at subsensory output (approx. 30 mA), for 30 minutes BIO. Polarity is alternated on a daily basis using Preset 64 pps, positive polarity. | |

FIG. 4D

Clinical Protocols

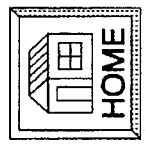

ULTRASOUND (page 1 of 24)

| Cervical | Freq | Mode | Time | Intensity W/cm2 | Rational |
|---|---|---|---|---|---|
| LIGAMENT SPRAIN | | | | | |
| Select — Acute | 1 or 3.3 | Pulsed 20% | 5 min | .2 - .5 | Nonthermal, micromassage |
| Select — Subacute | 1 or 3.3 | Pulsed 50% | 5 min | .5 - 1.0 | Minimize thermal |
| Select — Chronic | 1 or 3.3 | Continuous | 5 min | 1.0 - 1.5 | Mild to moderate thermal |
| MUSCLE SPASM | | | | | |
| Select — Acute | 1 or 3.3 | Pulsed 20% | 5 min | .5 - 1.0 | Nonthermal, micromassage |
| Select — Subacute | 1 or 3.3 | Pulsed 50% | 5 min | 1.0 - 1.5 | Mild thermal |
| Select — Chronic | 1 or 3.3 | Continuous | 5 min | 1.5 - 2.0 | Moderate to vigorous heating |

*FIG. 4E*

Stim Summary
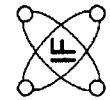
1 2 Interferential (P)
Lumbar Strains: Acute
Beat Freq
High : 150 Hz
Low : 80 Hz
Sweep: On
Time : 15.0 Sec
Amplitude Mod
Scan : On
Time : 10.0 sec
Percent: 40%
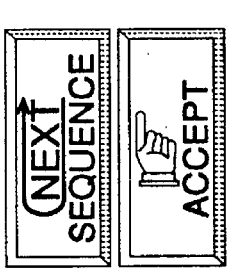
Carrier Freq
5000 Hz
Treatment Time
20 Min
 GO BACK    HELP    SAVE
| Channel 1 | Channel 2 | Channel 3 | Channel 4 | Ultrasound |
|---|---|---|---|---|
| 0 mA | 0 mA | 0 mA | 0 mA | 0.0 W/cm2 |
| 00:00 | 00:00 | 00:00 | 00:00 | Soundhd OK 00:00 |
FIG. 4G

Select Treatment
Protocol
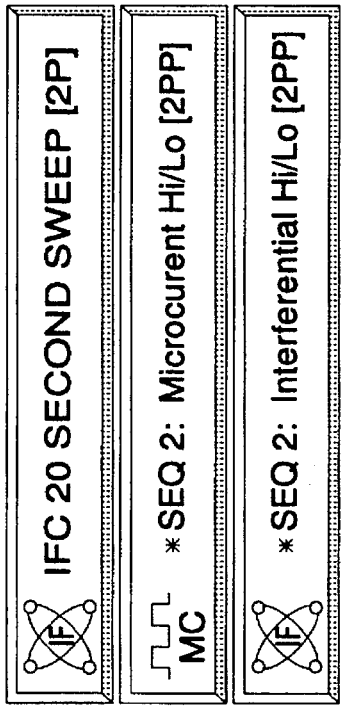
- IFC 20 SECOND SWEEP [2P]
- *SEQ 2: Microcurent Hi/Lo [2PP]
- *SEQ 2: Interferential Hi/Lo [2PP]
 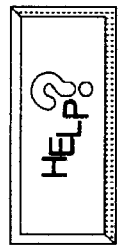
GO BACK    HELP
| Channel 1 | Channel 2 | Channel 3 | Channel 4 | Ultrasound |
|---|---|---|---|---|
| 0 mA | 0 mA | 0 mA | 0 mA | 0.0 W/cm2 |
| 00:00 | 00:00 | 00:00 | 00:00 | Soundhd OK 00:00 |
FIG. 4L

PHYSICAL THERAPY APPARATUS HAVING AN INTERACTIVE INTERFACE, AND METHOD OF CONFIGURING SAME

FIELD OF THE INVENTION

This invention relates generally to a physical therapy apparatus for applying a therapeutic treatment to a patient and, more particularly, to a physical therapy apparatus which is reconfigurable for treating a variety of physical ailments.

BACKGROUND OF THE INVENTION

Over the years, the popularity of less invasive procedures such as physical therapy have grown significantly. Various systems have been developed for applying a non-invasive therapeutic treatment to a patient such as for physical therapy. These systems generally may include therapeutic ultrasound units, electrical stimulation units, or a combination thereof. A therapeutic ultrasound unit, for example, employs a high frequency oscillator and a power amplifier to generate a high frequency electrical signal that is then delivered to a piezoelectric transducer housed in a handheld applicator. The transducer converts the electrical signal to ultrasonic energy at the same frequency. The ultrasonic energy is then transmitted to the patient by applying a radiating plate on the transducer against the patient's skin.

Of the total power of the electrical signal delivered to the transducer, only a portion is actually radiated to the patient's tissue as ultrasonic energy. The other portion of the total power is dissipated in the transducer and parts of the applicator in the form of heat. As the applicator is moved over a treatment site, the acoustic coupling to the patient's body changes which results in a change in the proportion of the power radiated to the patient relative to the power dissipated in the transducer. This coupling efficiency change is caused by changes in acoustic impedance as different types of tissue are encountered, and as air, whose acoustic impedance is much different than that of tissue, enters the space between the skin and the applicator.

Likewise, an electrical stimulation unit, for example, employs a high frequency oscillator and a power amplifier to generate a high frequency electrical signal that is then delivered to a transducer, such as an electrode. The electrical energy is then transmitted to the patient by applying a probe contact containing the electrode against the patient's skin. The amplitude of the electrical signal plays a significant role in these electrical stimulation systems because the lower the amplitude of the electrical signal, the more tolerant the patient is to the stimulation transmitted by the electrode.

During the use of these types of physical therapy systems, however, the amount of power, the frequency, and amplitude parameters, for example, may vary particularly depending on the particular physical ailment of the patient intended to be addressed by the physical therapist or user of the system. The different types of injuries and treatments for these injuries are numerous. Also, each treatment technique or procedure has numerous variations of the power, frequency, amplitude, treatment time and the like appropriate for the treatment procedure. Further, in order to provide the best rehabilitation or other therapeutic treatment, the physical therapy systems must be properly configured.

The physical therapist is therefore required to either memorize or have a reference manual handy to refer to various clinical protocol procedures and application procedures for use of the ultrasound or electrical stimulation system for these numerous types of physical ailments and then configure the system according to the protocol procedures. Systems have also been developed which save a protocol procedure for later reference once the user of the system enters the required application parameters and configures the system for a particular protocol procedure.

The burden on the physical therapist to remember the protocol procedures and the system application parameters for the procedures for the numerous physical ailments, to search a reference manual, to enter application parameters into a physical therapy system for configuration either initially for various systems desired to be used or continuously for each system is tremendous. These various options for the physical therapist are also time consuming, error prone, i.e., incorrect operational parameters entered by the physical therapist, and ultimately more costly to patients.

OBJECTS AND SUMMARY OF THE INVENTION

With the foregoing in mind, it is therefore an object of the present invention to provide a method and an apparatus for responsively reconfiguring a physical therapy apparatus based on predetermined physical ailments of a patient.

It is yet another object of the present invention to provide a method and an apparatus for reducing the number of specific operational parameters which an operator of a physical therapy apparatus must enter in order to configure a physical therapy apparatus.

It is a yet another object of the present invention to provide a reconfigurable physical therapy apparatus having an interactive user interface for selecting ailment protocols, treatment or application operational parameters associated with the protocol, and responsively reconfiguring the apparatus for the particular ailment desired to be therapeutically treated.

It is a further object of the present invention to provide a computer-controlled physical therapy apparatus.

These and other objects are provided, according to the present invention, by a reconfigurable physical therapy apparatus including an interactive ailment-protocol selection interface for responsively configuring the physical therapy apparatus. The interactive ailment-protocol selection interface preferably includes ailment storage means for storing identification data representative of at least one predetermined physical ailment for each of a plurality of human body parts and a corresponding set of transducer operational parameters associated with each predetermined physical ailment and each predetermined body part. Each set of transducer operational parameters preferably defines the therapeutic treatment provided by the physical therapy apparatus to thereby treat the predetermined physical ailment with which the set of transducer operational parameters is associated.

The interactive ailment-protocol selection interface also includes a screen display for displaying at least one of said identification data representative of a plurality of physical ailments which are associated with at least one of the identified human body parts. In addition, the interactive ailment-protocol selection interface includes ailment selecting means positioned in electrical communication with the ailment storage means and responsive to operator selection of one of the identified physical ailments which are associated with human body parts. The ailment selecting means obtains the set of transducer operational parameters associated with the selected physical ailment.

The reconfigurable physical therapy apparatus also includes a physical therapy applicator. The physical therapy applicator includes a transducer for applying a therapeutic treatment to a patient. For example, the physical therapy applicator preferably can be adapted to provide at least electrical stimulation, ultrasonic stimulation or both types of stimulation. The reconfigurable physical therapy apparatus further includes a transducer reconfiguring means, including a controller, positioned in electrical communication with the transducer and responsive to the ailment selecting means. The transducer reconfiguring means reconfigures the transducer to provide therapeutic treatment to the identified body part according to the obtained set of transducer operational parameters. Accordingly, the patient can then be preferentially treated for the physical ailment selected by the operator.

By configuring the transducer to provide a predetermined therapeutic treatment based upon the selection of a physical ailment associated with at least one of the body parts, the operator of the physical therapy apparatus need not individually enter each of the transducer operational parameters which, in turn, configure the transducer and define the resulting therapeutic treatment provided by the physical therapy apparatus. Instead, the transducer of the physical therapy applicator is responsively reconfigured based upon the set of transducer operational parameters associated with the physical ailment selected. Therefore, in addition to providing a more readily configurable physical therapy apparatus, the physical therapy apparatus of the present invention effectively reduces the possibility that an operator will improperly configure the physical therapy apparatus by inadvertently entering an incorrect parameter.

Each set of transducer operational parameters define a respective clinical protocol which, in turn, define the output or stimulation provided by the physical therapy apparatus. In addition, the set of transducer operational parameters associated with each predetermined physical ailment and each body part vary based upon the type of stimulation provided by the physical therapy applicator. For example, the set of transducer operational parameters for a physical therapy apparatus which includes an applicator adapted to provide electrical stimulation preferably include waveform type, number of channels, frequency, duty cycle, cycle time, amplitude modulation and treatment time. Alternatively, the set of transducer operational parameters for a physical therapy apparatus which preferably includes an applicator adapted to provide ultrasonic stimulation include frequency, number of channels, duty cycle and treatment time.

In one advantageous embodiment, the ailment storage means includes a memory device for storing the identification data representative of at least one predetermined physical ailment for each of a plurality of human body parts and the corresponding set of transducer operational parameters associated with each predetermined physical ailment and each predetermined body part. The memory device can include both a clinical protocol data file and a screen display data file. The clinical protocol data file includes the plurality of sets of transducer operational parameters which define the respective clinical protocols and the screen display data file includes data representative of the displayed information regarding each respective clinical protocol including data representative of the plurality of predetermined physical ailments.

In a further embodiment in which the physical therapy applicator is adapted to provide a plurality of types of predetermined stimuli including ultrasonic stimulation and various types of electrical stimulation, including pain management, muscle contraction, wound healing, the clinical protocol data file can include a plurality of subfiles. For example, the clinical protocol data file can include an ultrasound data file, a pain management data file, a muscle contraction data file and a wound healing data file. These subfiles include sets of transducer operational parameters which define the configuration of the transducer so as to provide ultrasound therapy, pain management, muscle contraction and wound healing, respectively. Accordingly, by subdividing the sets of transducer operational parameters into subfiles based upon the type of stimuli provided by the physical therapy apparatus, the physical therapy apparatus can readily access the sets of transducer operational parameters associated with the predetermined type of stimuli desired by the operator.

The interactive ailment-protocol selection interface can also include ailment sorting means for forming a subset from the identification data representative of the plurality of physical ailments based upon a predetermined criteria. For example, the predetermined criteria can be a specific type of physical ailment. Thus, the identification data displayed by the screen display preferably includes identification data selected from the subset. Accordingly, by appropriately sorting the identification data representative of the plurality of physical ailments, the number of physical ailments from which the operator must select can be significantly reduced, thereby facilitating the process of configuring the physical therapy apparatus.

The interactive ailment-protocol selection interface can also include modification means for modifying at least one transducer operational parameter of the set of transducer operational parameters associated with the selected physical ailment. Accordingly, the transducer can be reconfigured based upon the modified parameters, thereby modifying the therapeutic treatment provided by the transducer.

In addition, the identification data representative of a selected physical ailment can be stored in a selected treatment storage means. Thus, the operator of the physical therapy apparatus can readily select treatment of a physical ailment which has been previously selected and is stored in the selected treatment storage means without searching through the identification data representative of each of the physical ailments. The identification data stored in the selected treatment storage means can include identification data representative of physical ailments for which the operator has modified the associated set of transducer operational parameters.

According to another aspect of the present invention, a method of responsively reconfiguring a physical therapy apparatus is provided. The method includes the step of providing identification data representative of at least one physical ailment for each of a plurality of human body parts and a corresponding set of transducer operational parameters. At least one of the identification data representative of a physical ailment is then displayed such that an operator can select the physical ailment from among the displayed identification data for which the patient is desirably treated. The physical therapy apparatus can then be configured to provide a predetermined clinical protocol based upon the set of transducer operational parameters corresponding to the selected physical ailment. Thus, stimulation as defined by the clinical protocol can be provided to the patient to thereby specifically treat the selected physical ailment.

According to the present invention, the screen display can display identification data representative of a plurality of physical ailments. By selecting a displayed physical ailment, the set of transducer operational parameters associated with the selected physical ailment can be obtained and the transducer configured in response thereto. Accordingly, the transducer can provide the predetermined therapeutic treatment specified by the clinical protocol defined by the set of transducer operational parameters associated with the selected physical ailment. Due to the display of identification data representative of a plurality of physical ailments, the operator of the physical therapy apparatus can appropriately configure the transducer to treat a predetermined physical ailment by merely selecting the predetermined physical ailment. Thus, the operator need not tediously enter each transducer operational parameter in order to configure the transducer to provide a desired therapeutic treatment. Accordingly, the configuration of the physical therapy apparatus of the present invention to treat a specific physical ailment is not only simplified, but is also made more reliable due to the responsive configuration of the transducer based upon the selection of the specific physical ailment.

BRIEF DESCRIPTION OF THE DRAWINGS

Other objects and advantages will appear as the description proceeds when taken in connection with the accompanying drawings, in which:

FIGS. 4A–4L illustrate display screens which are presented to an operator during the configuration of a physical therapy apparatus according to the present invention.

DETAILED DESCRIPTION OF THE PREFERRED EMBODIMENT

The present invention now will be described more fully hereinafter with reference to the accompanying drawings in which preferred embodiments of the invention are shown. This invention may, however, be embodied in many different forms and should not be construed as limited to the illustrated embodiments set forth herein; rather, these illustrated embodiments are provided so that this disclosure will be thorough and complete and will fully convey the scope of the invention to those skilled in the art. Like numbers refer to like elements throughout.

Figure 1:
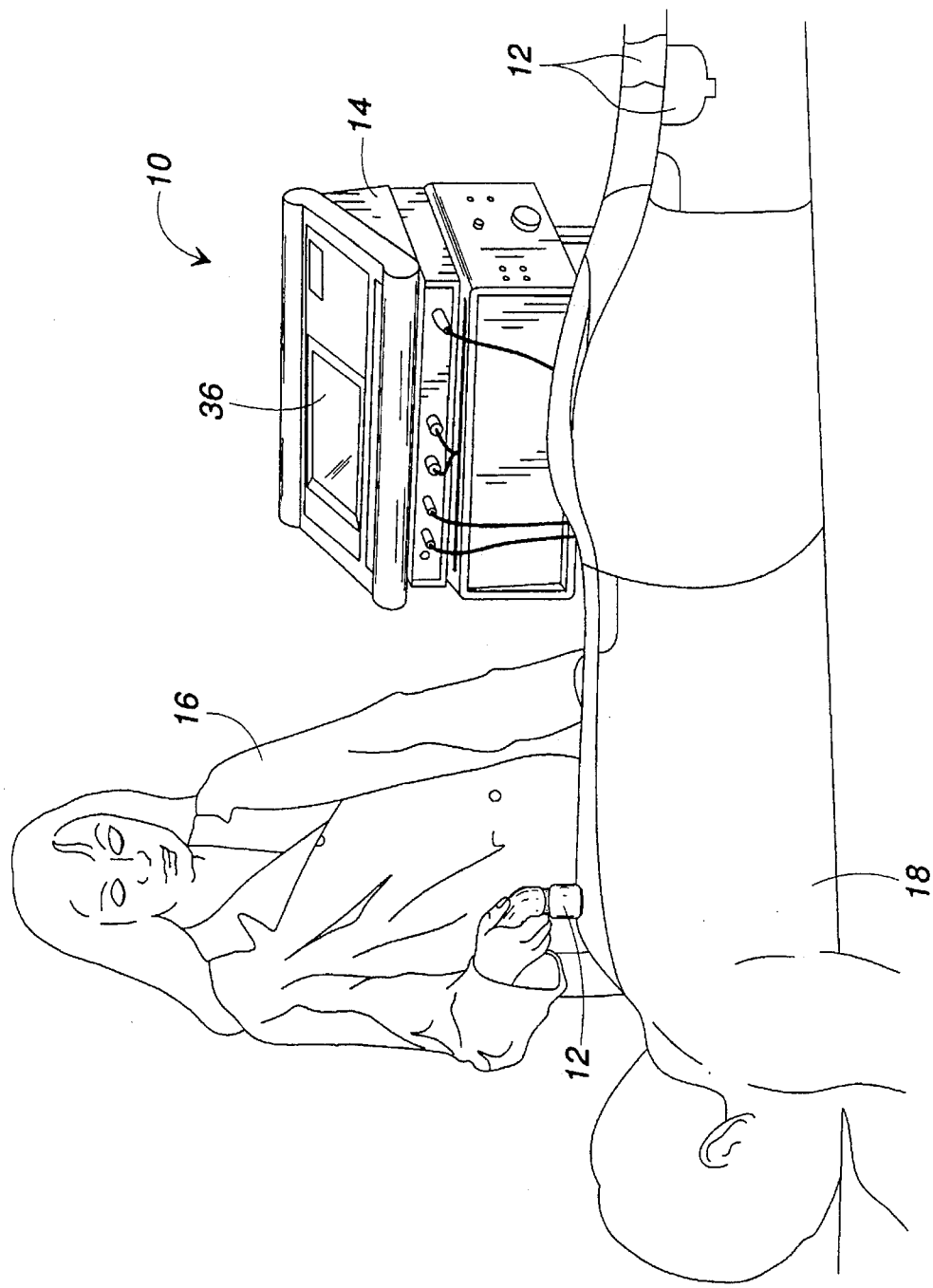
FIG. 1 is an environmental view of a physical therapy apparatus according to the present invention.

Referring now to FIG. 1, a physical therapy apparatus 10 according to one embodiment of the present invention is illustrated. The physical therapy apparatus can include a neuromuscular stimulating device which includes a physical therapy applicator 12 having at least one transducer 12a for applying therapeutic treatment to a patient 18. As used herein, transducer 12a includes not only an ultrasound transducer as shown in FIG. 1 within the physical therapy applicator 12, but also the electrodes 12' which deliver electrical stimulation to a patient. The physical therapy applicator can be adapted to provide one or more of a plurality of types of predetermined stimuli. For example, the physical therapy applicator can provide electrical stimulation, ultrasonic stimulation, or both electrical and ultrasonic stimulation as known to those skilled in the art.

The physical therapy apparatus 10 of FIG. 1 also includes a base unit 14 positioned in communication, typically electrical communication, with the transducer 12a of the physical therapy applicator 12. While the physical therapy applicator is electrically connected to the base unit via one or more electrical cables in FIG. 1, the base unit and the physical therapy applicator can communicate according to a variety of electrical and optical communication methods known to those skilled in the art. In addition, while a relatively large physical therapy apparatus is shown in FIG. 1, the physical therapy apparatus can be much smaller so as to be portable without departing from the spirit and scope of the present invention.

According to the present invention, the base unit 14 includes an interactive ailment-protocol selection interface for providing a responsive interface with an operator 16 of the physical therapy apparatus 10. As will be apparent to those skilled in the art, the interactive ailment-protocol selection interface is preferably implemented by a combination of hardware and software. In addition, the various components of the interactive ailment-protocol selection interface described below preferably communicate via electrical command signals, however, other types of communication can be employed without departing from the spirit and scope of the present invention.

Figure 2A:
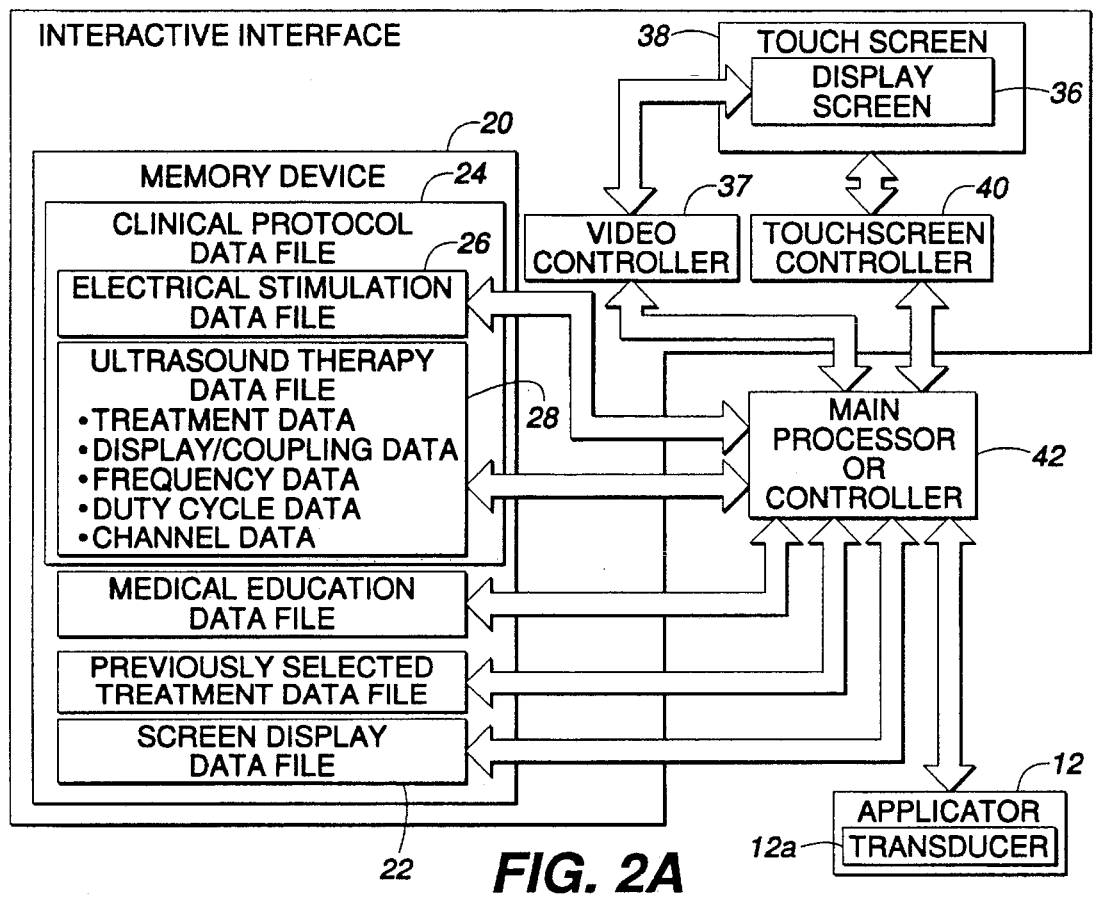
FIG. 2A is a schematic block diagram illustrating a physical therapy apparatus including the interactive ailment-protocol selection interface according to the present invention.

As illustrated schematically in FIG. 2A, the interactive ailment-protocol selection interface includes ailment storage means, including a memory device 20, for storing identification data representative of at least one physical ailment for each of a plurality of human body parts, such as an acute cervical sprain having well localized pain. The identification data stored by the ailment storage means also includes corresponding sets of transducer operational parameters associated with each predetermined physical ailment and each predetermined body part and defining respective clinical protocols. As described in detail hereinafter, the sets of transducer operational parameters and, more particularly, the clinical protocols define the configuration of the transducer such that the transducer provides a predetermined therapeutic treatment to a patient 18. Preferably, the set of transducer operational parameters is selected such that the resulting therapeutic treatment provided by the transducer is particularly adapted to treat the physical ailment associated with the set of transducer operational parameters.

The set of transducer operational parameters can include a variety of transducer operational parameters based upon the type of therapeutic treatment to be provided by the transducer. For example, for an applicator 12 adapted to provide electrical stimulation, the sets of transducer operational parameters typically define the waveform type, number of channels, frequency, duty cycle, amplitude modulation, cycle time data and treatment time. Alternatively, for an applicator adapted to provide ultrasonic stimulation, the sets of transducer operational parameters typically define the frequency, number of channels, duty cycle, treatment time and display/coupling data.

While the value of the parameters varies based upon the type of treatment associated therewith, a few exemplary parameter ranges are provided hereinbelow for solely purposes of illustration. For example, the waveform type is generally selected from interferential, premodulated, microcurrent, monophasic, Russian, VMS and VMS burst and the number of channels is typically one, two or four depending of the desired type of treatment. In addition, the frequency for ultrasonic stimulation is generally between about 1 MHz and about 3.3 MHz, while the frequency for electrical stimulation is typically between about 1 Hz and about 20 KHz. The treatment time also typically varies between about 5 minutes and about 20 minutes, but can be a variety of other lengths of time as known to those skilled in the art. Further, the duty cycle of the stimuli is typically between about 1% and about 20%. As described above, however, each of the parameters can have a variety of other values depending upon the desired type of treatment without departing from the spirit and scope of the present invention.

Figure 2B:
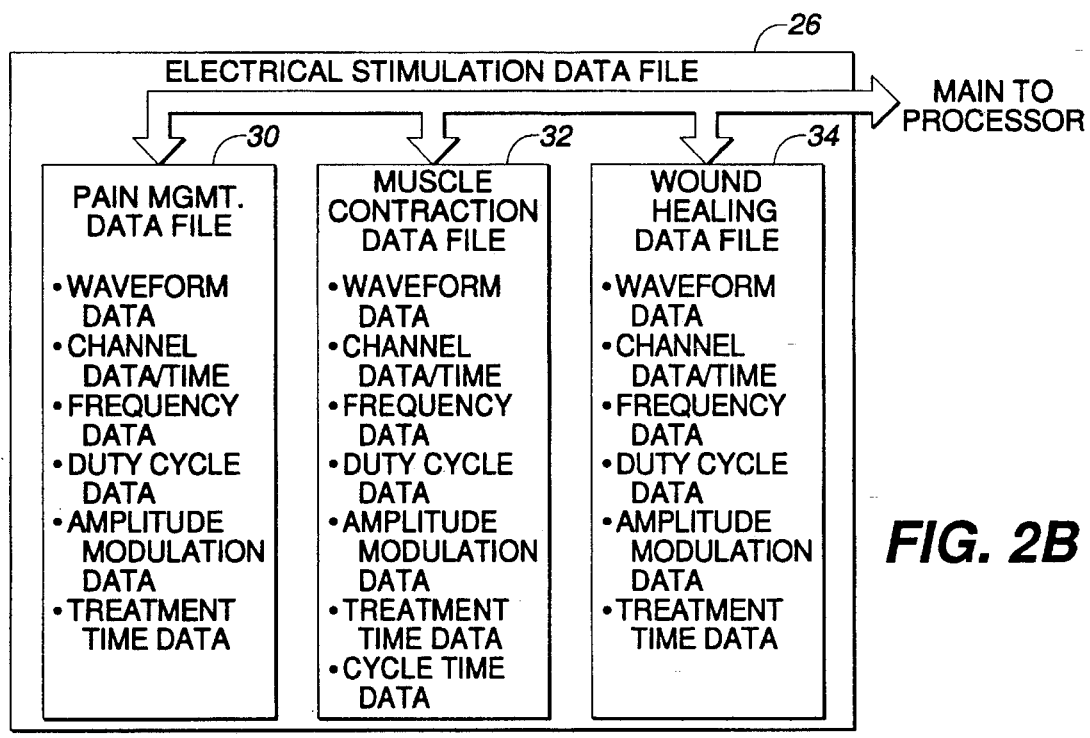
FIG. 2B is a schematic block diagram of the electrical stimulation data file of the memory device of the interactive ailment-protocol selection interface according to the present invention.

The ailment storage means and, in the embodiment illustrated in FIGS. 2A and 2B, the memory device 20 preferably stores the identification data including the sets of transducer operational parameters in a number of different data files. For example, the memory device can store the identification data representative of the displayed information regarding each physical ailment and each body part and, in some embodiments, information regarding the respective clinical protocol suggested for the displayed physical ailment in a screen display data file 22. In addition, the memory device can store the plurality of sets of transducer operational parameters in a clinical protocol definition file 24.

As further illustrated in FIG. 2A, the clinical protocol definition file 24 can be divided into an electrical stimulation data file 26 and an ultrasound therapy data file 28. The electrical stimulation data file and the ultrasound therapy data file include the clinical protocols and, more specifically, the sets of transducer operational parameters which configure the transducer to provide electrical stimulation and ultrasound therapy, respectively. As illustrated in FIG. 2B, the electrical stimulation data file can be further subdivided based upon the type of electrical stimulation for which the sets of transducer operational parameters configure the transducer. For example, the electrical stimulation data file can be subdivided into a pain management data file 30, a muscle contraction data file 32 and a wound healing data file 34. The pain management data file, the muscle contraction data file and the wound healing data file include sets of transducer operational parameters which configure the transducer to deliver electrical stimulation which provides pain management, muscle contraction and wound healing, respectively.

As also shown in FIGS. 2A and 2B, the sets of transducer operational parameters stored in the clinical protocol definition file 24 typically include the parameters for configuring the transducer, as described above. The clinical protocol definition file, however, can include sets of transducer operational parameters which have additional parameters to more particularly configure the transducer so as to provide a desired therapeutic treatment without departing from the spirit and scope of the present invention.

The physical therapy apparatus 10 and, more particularly, the interactive ailment-protocol selection interface can include a screen display 36 and an associated video controller 37 as illustrated in FIG. 1 and schematically in FIG. 2A. In one embodiment, the screen display is a VGA liquid crystal display screen. The screen display, however, can include other types of display screens without departing from the spirit and scope of the present invention. As explained in detail hereinafter, the screen display is responsive to the ailment storage means for displaying at least one of the identification data representative of a plurality of physical ailments which are associated with at least one of the identified human body parts.

In order to properly configure the transducer of the physical therapy applicator 12, the interactive ailment-protocol selection interface also includes ailment selecting means positioned in electrical communication with the ailment storage means and responsive to operator selection of one of the identified physical ailments. Based upon the operator selection, the ailment selecting means obtains the set of transducer operational parameters associated with the selected physical ailment so as to thereby the clinical protocol according to which the transducer will be configured.

In the embodiment illustrated in FIG. 2A, the ailment selecting means can include a touch screen 38 which overlies the display screen 36 such that the operator 16 of the physical therapy apparatus 10 can select a physical ailment by touching the screen at a designated location. In the illustrated embodiment, the ailment selecting means also includes a touch screen controller 40, responsive to the touch screen, for creating the X and Y coordinates which correspond to the location touched by the operator. In addition, the ailment selecting means can include a main controller 42 for determining the specific physical ailment selected by the operator based upon the X and Y coordinates generated by the touch screen controller. In turn, the main controller can obtain the set of transducer operational parameters associated with the selected physical ailment from the ailment storage means.

The operation of the main controller 42 is preferably controlled by a stored programming code. In one embodiment, the programming code preferably is written in $C^{++}$ programming language. The operations of the main controller, however, can be controlled by other types of programming code and languages known to those skilled in the art without departing from the spirit and scope of the present invention.

Although ailment selecting means which includes a touch screen 36 and an associated touch screen controller 38 is illustrated and described herein, the specific physical ailment can be selected in a variety of other manners without departing from the spirit and scope of the present invention. For example, the interactive ailment-protocol selection interface can include a keypad, a mouse, a light pen or other selection means known to those skilled in the art for selecting one of the physical ailments displayed by the screen display 36.

The physical therapy apparatus 10 of one embodiment also includes transducer reconfiguring means, typically including the main controller or processor 42, positioned in electrical communication with the transducer and responsive to the ailment selecting means. The transducer reconfiguring means reconfigures the transducer to provide therapeutic treatment to the identified body part according to the obtained set of transducer operational parameters. In one embodiment, the transducer reconfiguring means reconfigures the transducer by providing predetermined signals to the transducer indicative of the stimuli to be produced thereby. As understood by those skilled in the art, various techniques of implementing the operational and driving characteristics, i.e., oscillators, power amplifiers, transformers, analog-to-digital computers, of the transducer may be implemented to responsively operate the transducer from the controller. Accordingly, the transducer can provide a therapeutic treatment which is tailored to specifically treat the selected physical ailment.

Figure 3A:
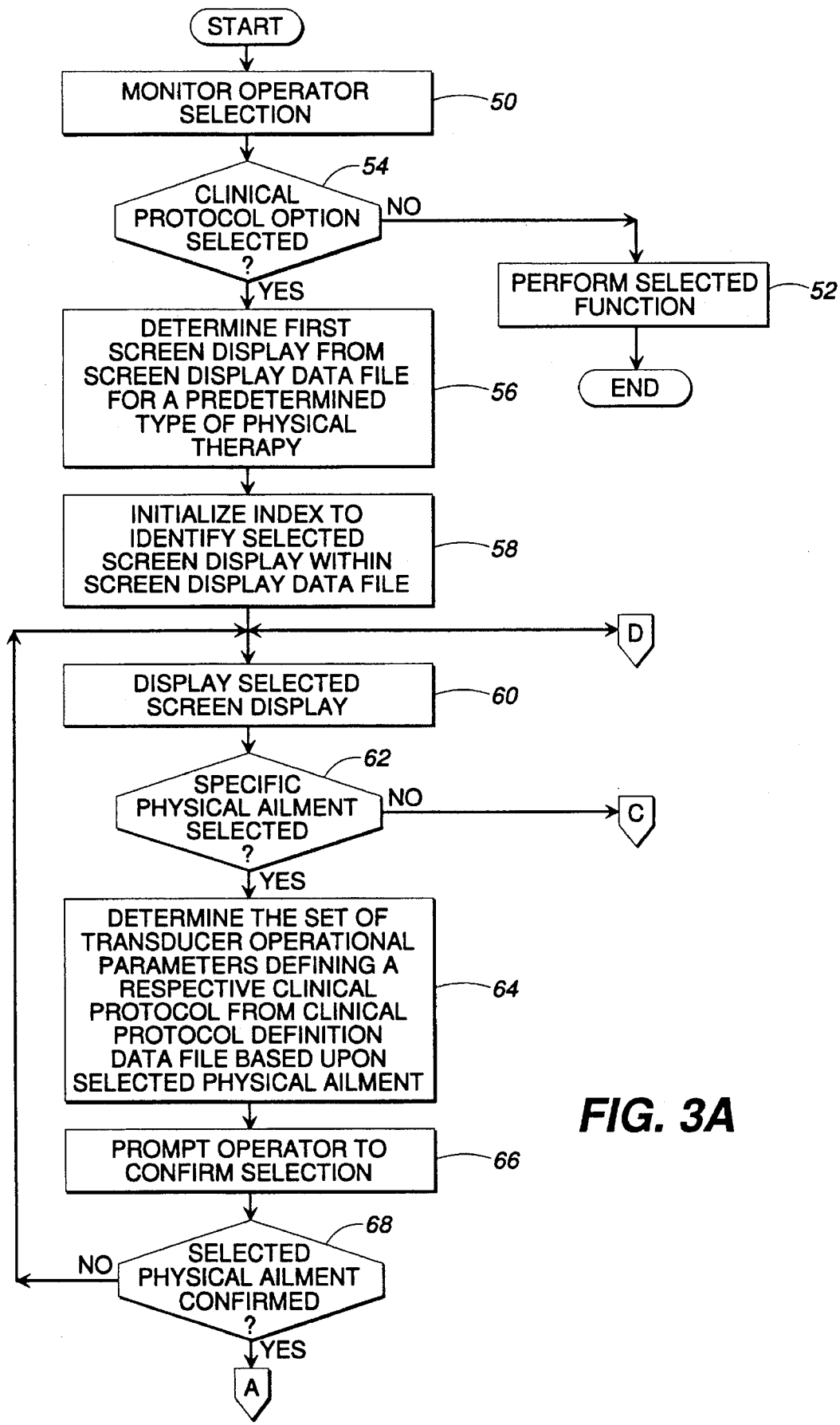
FIGS. 3A–3C are flow charts illustrating operations for responsibly configuring a physical therapy apparatus according to the present invention.
Figure 3B:
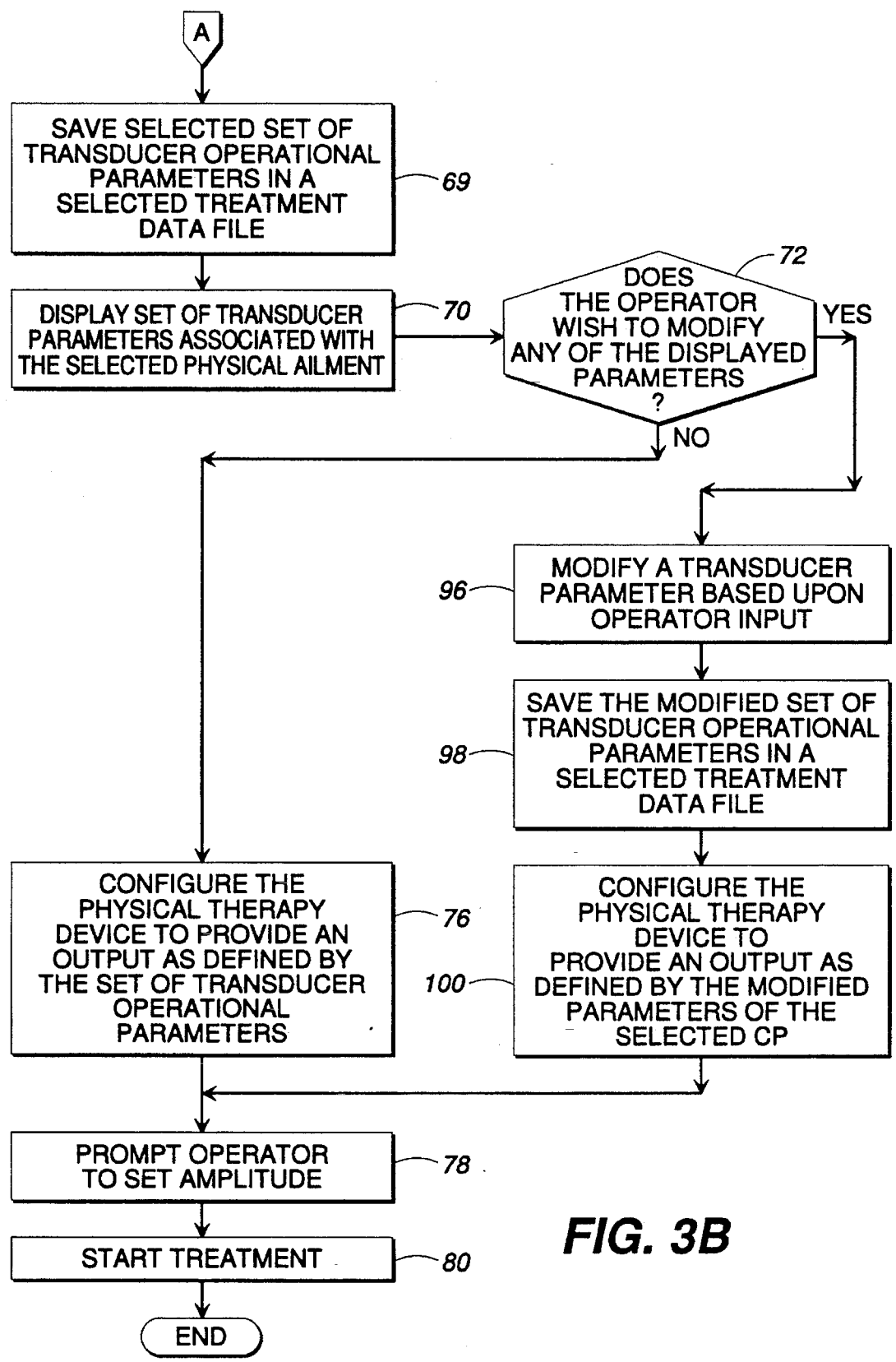
Figure 3C:
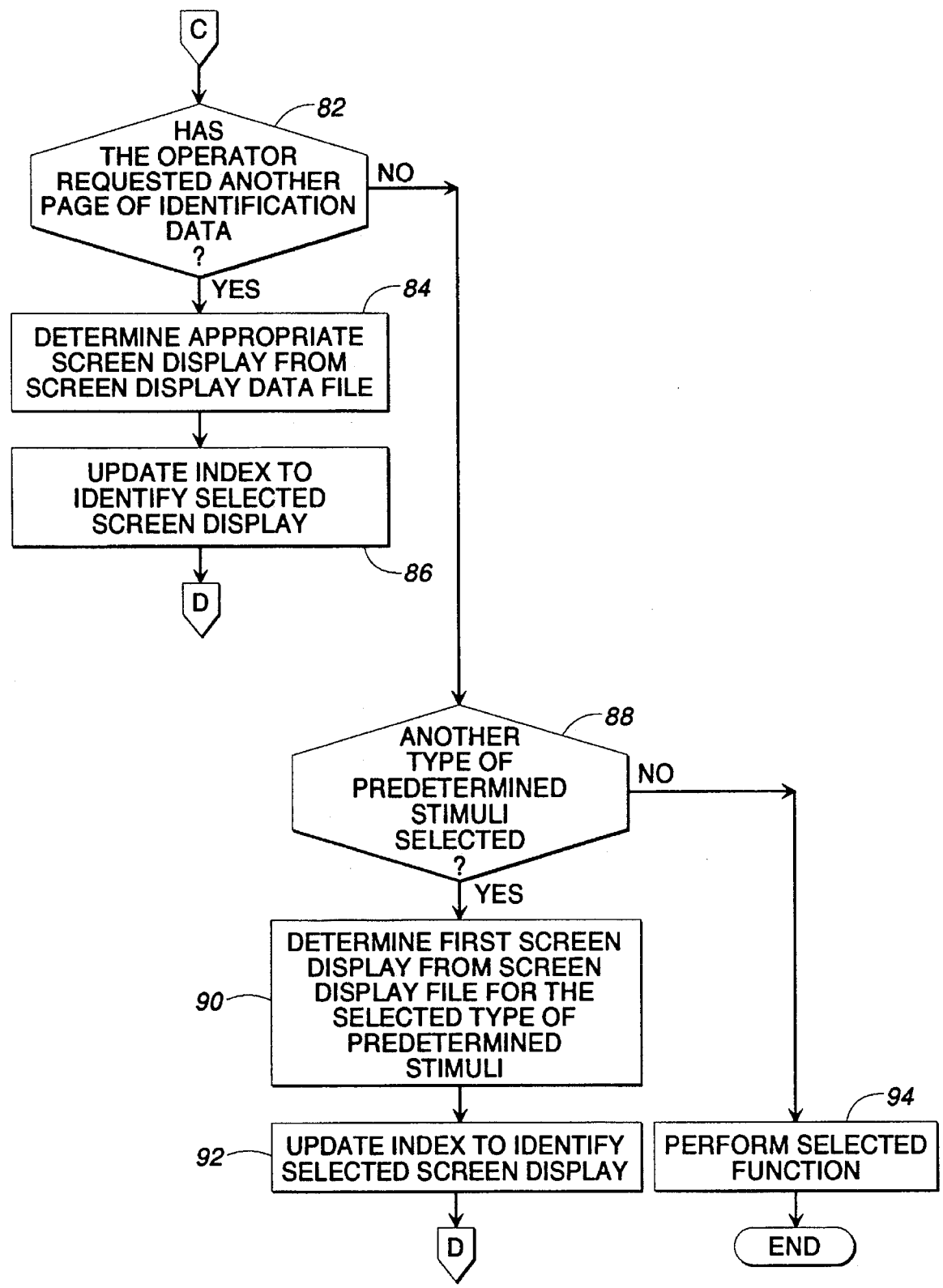
Figure 4A:
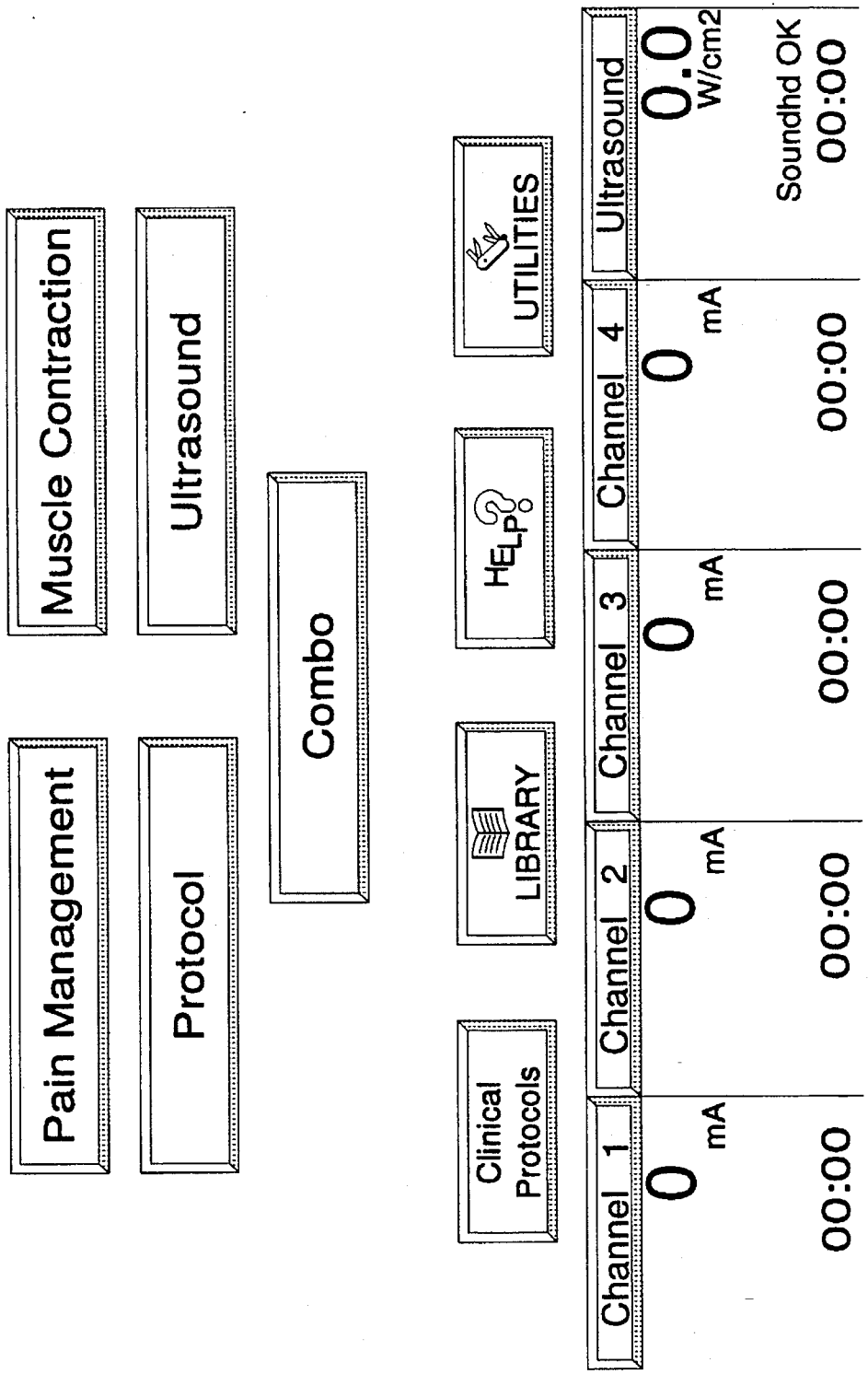

In operation as illustrated in FIGS. 3A–3C, the operator 16 of a physical therapy apparatus 10 of the present invention can readily reconfigure the transducer of the physical therapy applicator 12 based upon the specific physical ailment from which the patient 18 suffers. In one embodiment, a main menu screen is initially displayed on the display screen 36. As shown in FIG. 4A, the main menu screen prompts the operator to select the desired feature. For example, the selections can include pain management, muscle contraction and ultrasound which allow the operator to sequentially define each of the transducer operational parameters required to appropriately configure the transducer to provide the selected type of treatment, such as pain management, muscle contraction or ultrasound therapy. In addition, the operator can select the "COMBO" feature which allows the operator to configure the physical therapy apparatus 10 to simultaneously provide both electrical stimulation and ultrasound therapy as known to those skilled in the art.

The main menu screen of FIG. 4A also allows the operator 16 to select the help, utilities and library features which respectively provide operator assistance, which provide a number of predetermined utility features and which allows the operator to access on-line medical information. For example, the on-line medical information can include a variety of information relating to the various therapeutic treatments which the physical therapy apparatus 10 is adapted to provide. In addition, as shown in FIG. 2A, the memory device 20 can include a medical information data base 44 which stores data representative of the medical information provided by the library feature.

The main menu also provides a "protocol" function. By selecting the "protocol" function, a menu of previously selected sets of transducer operational parameters is displayed as shown in FIG. 4L. Thus, the operator 16 of the physical therapy apparatus 10 can rapidly reconfigure the transducer according to a previously selected set of transducer operational parameters. The "protocol" function is particularly useful in instances in which the transducer is repeatedly configured according to the same set of transducer operational parameters. For example, a physical therapy patient 18 may receive the same treatment every week. Accordingly, the set of transducer operational parameters which configure the transducer to provide this treatment can be stored, such as in a previously selected treatment data file 46 in the memory device 20 as shown in FIG. 2A. Thereafter, by merely renewing the selection of the set of transducer operational parameters following invocation of the "protocol" function, the transducer can be repeatedly reconfigured to provide the desired therapeutic treatment to the patient 18.

In operation, the physical therapy apparatus 10 and, in particular, the main controller 42 and the touch screen controller 40 monitor the touch screen 38 to determine which feature has been selected from the main menu screen as shown in block 50 in FIG. 3A. Once one of the features described above is selected, the selected feature is performed as described above and as illustrated in block 52. As shown in blocks 54 and 56, however, if the clinical protocol option is selected, the main controller 42 obtains identification data representative of at least one physical ailment for each of a plurality of human body parts, such as from the screen display data file 22 maintained by the memory device 20. In addition, the main controller preferably establishes an index to identify or mark the identification data which has been obtained, such as from the screen display data file, as shown in block 58. Thereafter, the identification data is displayed by the screen display 36 as illustrated in block 60 of FIG. 3A.

For example, a screen display which illustrates the display of identification data is shown in FIG. 4B. As illustrated, the identification data can include a description of the physical ailment, such as an acute cervical strain with well localized pain. In addition, the identification data can include a description of one or more of the transducer operational parameters suggested for appropriately configuring the transducer to treat the associated physical ailment. The identification data, however, need not include a description of the suggested transducer operational parameters since the operator 16 configures the physical therapy apparatus 10 based upon the physical ailment of the patient 18. As illustrated in FIG. 4B, the screen display can also include an indication of the type of stimulation, such as electrical stimulation for pain management, provided by the displayed selections.

Figure 4F:

As shown in blocks 62 and 64 of FIG. 3A, the interactive ailment-protocol selection interface determines if one of the displayed physical ailments has been selected and, if so, obtains the set of transducer operational parameters associated with the selected physical ailment, such as from the clinical protocol data file 24 as described above, to thereby defined the corresponding clinical protocol. Thereafter, the operator 16 is preferably prompted to confirm the selected physical ailment as shown in blocks 66 and 68, such as by a screen display as shown in FIG. 4F. If the operator fails to confirm the selection, the previously displayed identification data, such as shown in FIG. 4B, is again displayed in order to provide the operator with an opportunity to select another physical ailment for treatment.

Figure 4H:
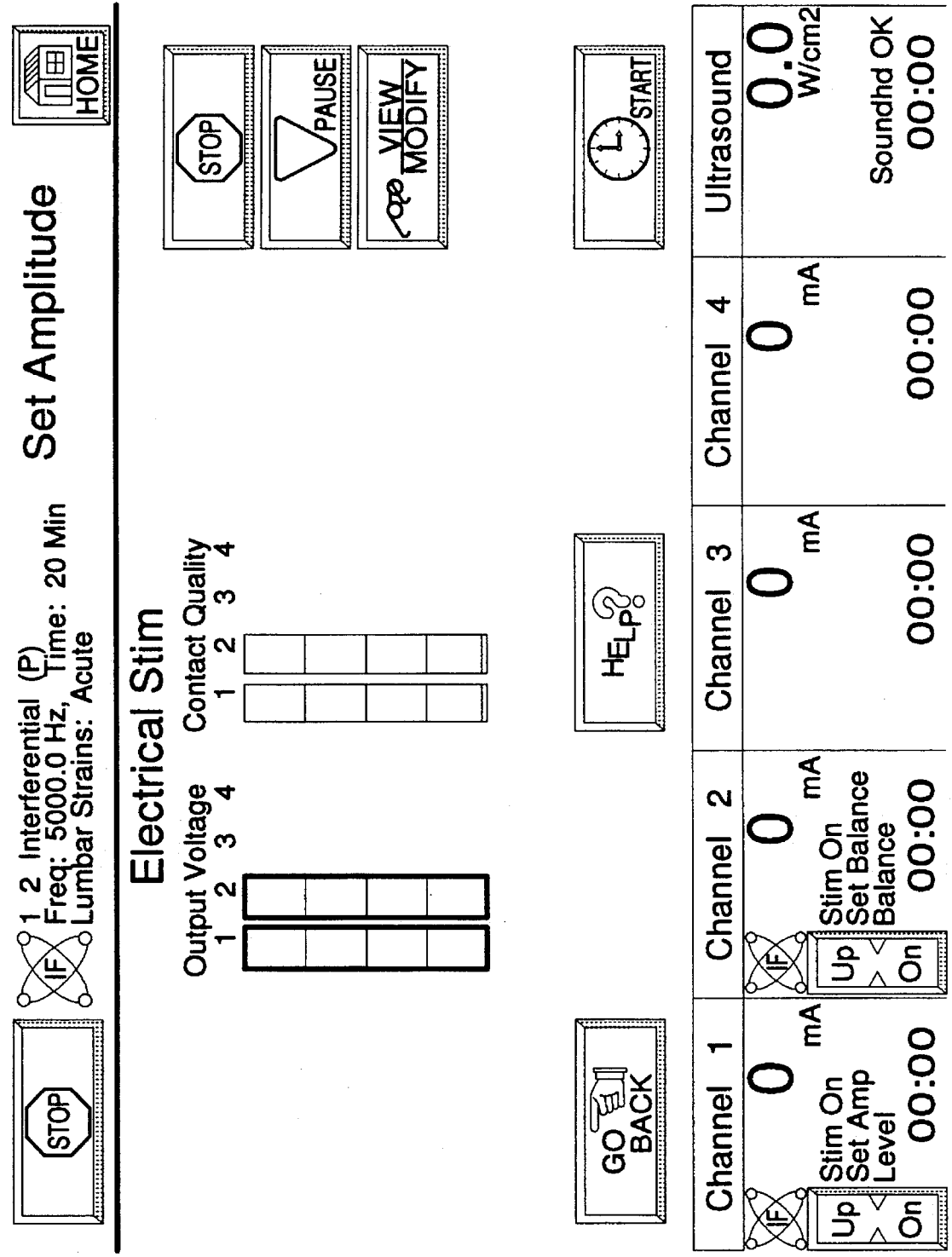
Figure 41:
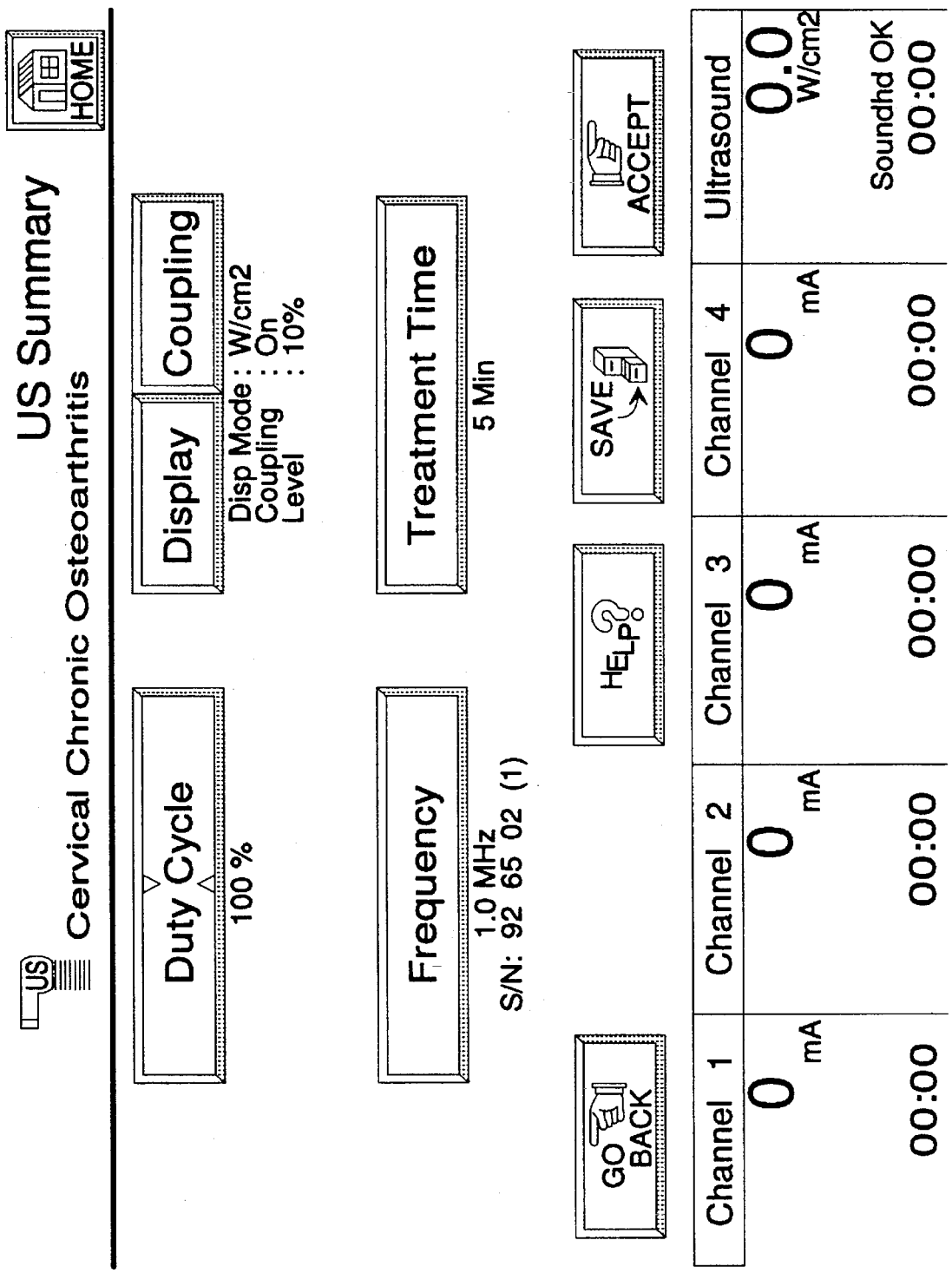
Figure 4J:
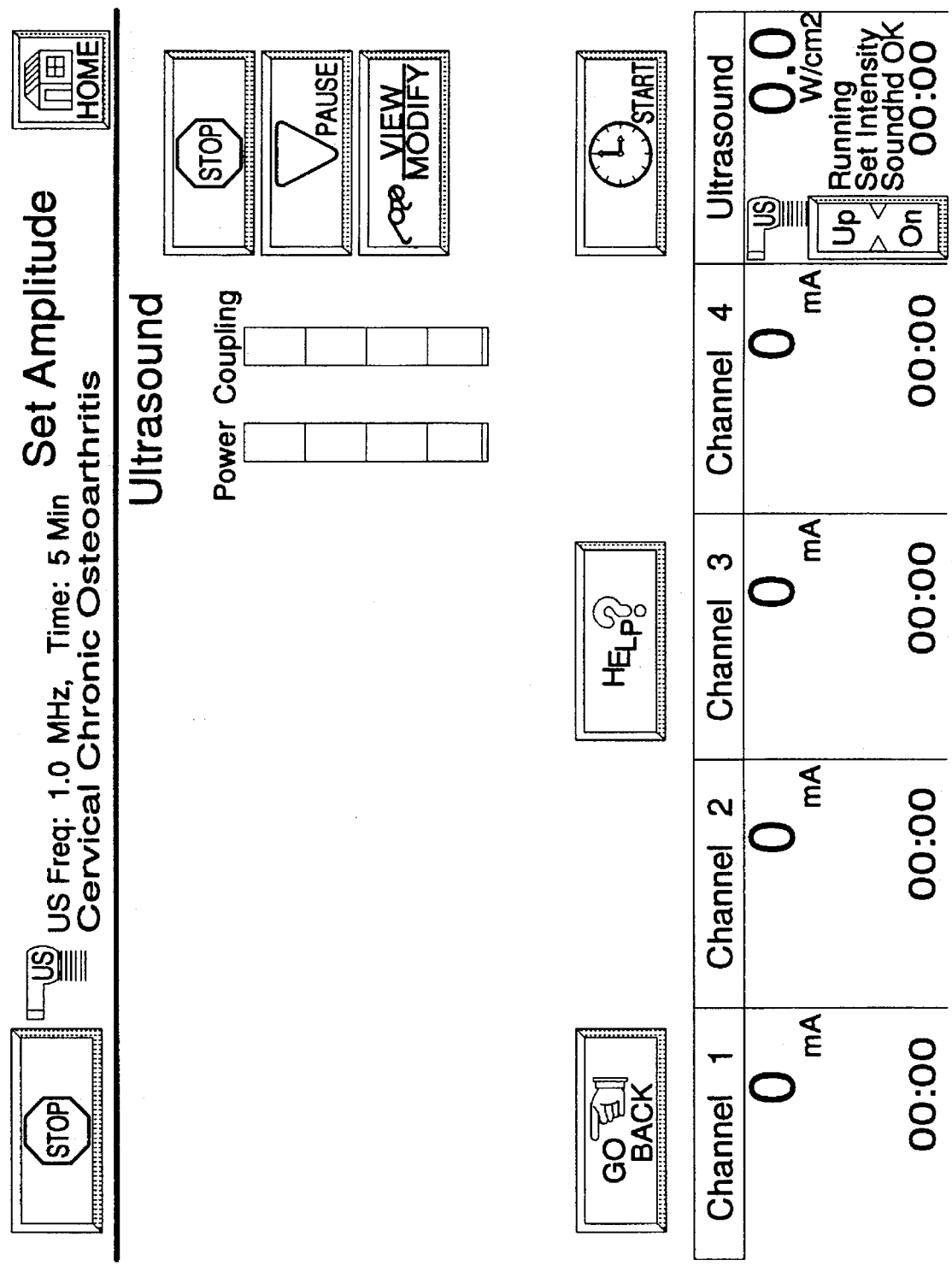
Figure 4K:
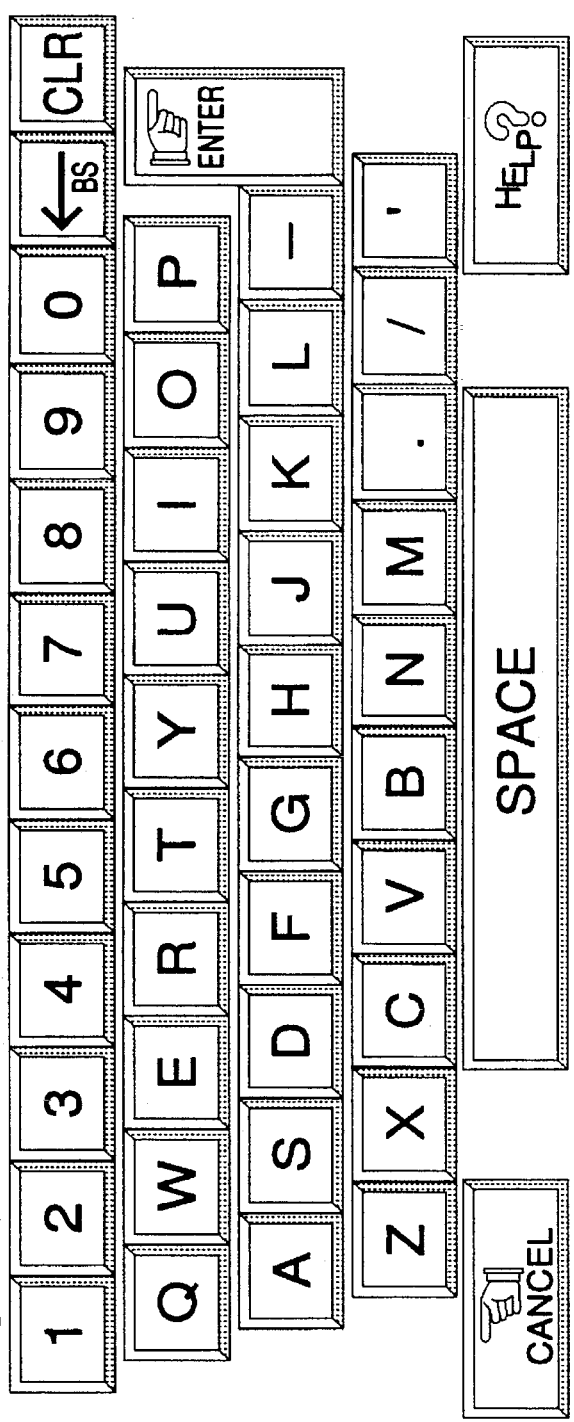

If the operator 16 does confirm the selection of the physical ailment, the set of transducer operational parameters can be named, if desired, as shown in FIG. 4K, and stored in the previously selected protocol data file 46, as shown in block 69 in FIG. 3B, such that the operator can readily renew their selection by selecting the "protocol" option as described above. In addition, the set of transducer operational parameters associated with the selected physical ailment can be displayed as shown in block 70 of FIG. 3B. Exemplary screen displays which define the set of transducer operational parameters associated with the selected physical ailment are shown in FIGS. 4G and 4I. In particular, FIG. 4G illustrates a set of transducer operational parameters which configure a transducer to provide electrical stimulation and FIG. 4I illustrates a set of transducer operational parameters which configure a transducer to provide ultrasonic stimulation.

As illustrated in blocks 72 and 76, if the operator 16 accepts the set of transducer operational parameters by declining to modify the transducer operational parameters as described hereinafter, the transducer reconfiguring means reconfigures the transducer such that the transducer is capable of providing therapeutic treatment to the identified body part according to the protocol defined by the accepted set of transducer operational parameters.

As shown block 78 and in FIGS. 4H and 4J, the operator 16 is also preferably prompted to select the amplitude of the stimulation to be provided by the transducer. For example, in FIG. 4H, the operator is prompted to select the output voltage of the electrical stimulation to be provided by the transducer while, in FIG. 4J, the operator is prompted to select the power of the ultrasonic stimulation to be provided by the transducer. In either embodiment, once the amplitude has been selected, the therapeutic treatment defined by the set of transducer operational parameters associated with the selected physical ailment can be initiated as shown in block 80. In addition, while the interactive ailment-protocol selection interface of this embodiment of the present invention prompts the operator to select the amplitude of the stimuli to be delivered by the transducer, the amplitude can be one of the predefined transducer operational parameters which correspond with respective ones of the displayed physical ailments without departing from the spirit and scope of the present invention.

If the operator 16 does not select one of the displayed physical ailments, the interactive ailment-protocol selection interface determines if the operator has requested that another page of identification data be displayed, such as by selecting "next page" or "previous page", as shown in block 82 of FIG. 3C. If the operator has selected another page of identification data, the main controller 42 determines the appropriate identification data to be displayed based, at least in part, upon the index identifying the memory location of the previously displayed identification data as illustrated in block 84. Thereafter, the main controller updates the index and displays the appropriate identification data as shown in blocks 86 and 60. Accordingly, the operator can sequentially page through the identification data representative of the plurality of physical ailments for each of the plurality of human body parts.

Alternatively, if the operator 16 does not select one of the displayed physical ailments and does not request that another page of the identification data be displayed, the interactive ailment-protocol selection interface determines if the operator has selected another type of predetermined stimuli as shown in block 88. As described above, the physical therapy apparatus 10 can provide ultrasonic stimulation, electrical stimulation or both ultrasonic and electrical stimulation. In addition, the electrical stimulation can be provided for a variety of purposes including pain management, muscle contraction and wound healing. Accordingly, identification data can be displayed based upon the type of predetermined stimuli with which the identification data is associated. For example, identification data representative of various physical ailments which are treated with a pain management technique, a muscle contraction technique, a wound healing technique and by ultrasound therapy are illustrated in FIGS. 4B, 4C, 4D and 4E, respectively. As also shown in FIGS. 4B–4E, the operator can selectively display identification data associated with a predetermined type of stimuli by selecting an icon corresponding to the predetermined type of stimuli.

Accordingly, if the operator 16 selects another type of predetermined stimuli other than the type of stimuli associated with the displayed identification data, such as by selecting the icon associated with another desired type of stimuli, the interactive ailment-protocol selection interface obtains and displays identification data associated with the desired type of stimuli and updates the index accordingly, as shown in blocks 90, 92 and 60. If the operator does not select another type of predetermined stimuli, but, instead, selects another option, such as the "go back" option, the physical therapy apparatus and, more particularly, the interactive ailment-protocol selection interface performs the selected function as shown in block The interactive ailment-protocol selection interface can also include modification means for modifying at least one transducer operational parameter of the set of transducer operational parameters associated with the selected physical ailment. In one embodiment, the modification means includes the main controller 42, however, the modification means can be comprised of a variety of other types of hardware and/or software, including a modifier, separate from the main controller, without departing from the spirit and scope of the present invention. In the exemplary embodiment illustrated in blocks 72 and 96 of FIGS. 3A and 3B, the set of transducer operational parameters can be modified prior to accepting the displayed set of transducer operational parameters. Accordingly, the transducer can be reconfigured based upon the protocol defined by the modified parameters, thereby modifying the therapeutic treatment provided by the transducer as illustrated in block 100. In addition, the modified set of transducer operational parameters can be stored, if desired, in the previously selected treatment data file 46 as described above and as shown in block 98 such that the modified set of transducer operational parameters can be readily accessed without requiring the operator 16 to recreate the modified set of transducer operational parameters.

The interactive ailment-protocol selection interface of one embodiment also includes ailment sorting means for forming a subset from the identification data representative of the plurality of physical ailments based upon a predetermined criteria. In one embodiment, the ailment sorting means includes the main controller 42, however, the ailment sorting means can be comprised of a variety of other types of hardware and/or software, such as ailment sorter, separate from the main controller, without departing from the spirit and scope of the present invention. For example, the predetermined criteria can include a predetermined body part such that the identification data included within the subset is representative of various physical ailments for the predetermined body part. Further, in one advantageous embodiment, the screen display 36 can display a human body and prompt the operator 16 to select the body part, such as by touch the touch screen 38 which defines the criteria according to which the identification data will be sorted. Alternatively, the predetermined criteria can include a specific type of physical ailment.

Thus, in this embodiment, the operator 16 can create a subset of identification data based on a predetermined criteria prior to displaying the identification data. Consequently, the identification data thereafter displayed can be selected from the subset of identification data. Accordingly, by appropriately sorting the identification data representative of the plurality of physical ailments, the number of physical ailments from which the operator must select can be significantly reduced, thereby facilitating the process of configuring the physical therapy apparatus 10.

By configuring the transducer to provide a predetermined therapeutic treatment based upon the selection of a physical ailment associated with at least one of the body parts, the operator 16 of the physical therapy apparatus 10 need not sequentially enter each of the transducer operational parameters which, in turn, configure the transducer and define the resulting therapeutic treatment provided by the physical therapy apparatus. Instead, the transducer of the physical therapy applicator is responsively reconfigured based upon the set of transducer operational parameters associated with the physical ailment selected. Therefore, in addition to providing a more readily configurable physical therapy apparatus, the physical therapy apparatus of the present invention effectively reduces the possibility that an operator will improperly configure the physical therapy apparatus by inadvertently entering an incorrect parameter.

In the drawings and specification, there have been disclosed typical preferred embodiments of the invention, and, although specific terms are employed, these terms are used in a descriptive sense only and not for purposes of limitation. The invention has been described in considerable detail with specific reference to various illustrated embodiments. It will be apparent, however, that various modifications and changes can be made within the spirit and scope of the invention as described in the foregoing specification and defined in the appended claims.

The invention claimed is:

1. A reconfigurable physical therapy apparatus comprising:

a physical therapy applicator including a transducer for applying a therapeutic treatment to a patient;

transducer reconfiguring means operatively connected in electrical communication with said transducer of said applicator for selectively reconfiguring operational parameters of said transducer of said applicator; and an interactive ailment-protocol selection interface operatively connected in electrical communication with said transducer reconfiguring means, said interactive ailment-protocol selection interface including:

ailment storage means for storing identification data representative of at least one predetermined physical ailment for each of a plurality of predetermined human body parts and a corresponding set of predetermined transducer operational parameters associated with each predetermined physical ailment and each predetermined body part so as to define a respective clinical protocol, a screen display responsive to said ailment storage means for displaying identification data representative of at least one physical ailment for at least one of the predetermined human body parts, and ailment selecting means, operatively connected in electrical communication with said ailment storage means and responsive to operator selection of one of the physical ailments for which representative identification data is displayed, for obtaining the set of predetermined transducer operational parameters associated with the selected physical ailments, wherein said transducer reconfiguring means is responsive to said ailment selecting means for automatically reconfiguring the operational parameters of said transducer based upon the set of transducer operational parameters obtained by said ailment selecting means to provide therapeutic treatment to the identified body part according to the obtained transducer operational parameters.

2. A reconfigurable physical therapy apparatus as defined in claim 1, wherein said physical therapy applicator comprises an electrical stimulation applicator means for providing predetermined electrical stimuli to the patient based upon the selected physical ailment.

3. A reconfigurable physical therapy apparatus as defined in claim 2, wherein the predetermined electrical stimuli are defined by a clinical protocol having the predetermined set of transducer operational parameters, the predetermined set of transducer operational parameters being selected from the group consisting of waveform type, number of channels, frequency, duty cycle, amplitude modulation, cycle time and treatment time, and wherein said ailment storage means comprises a memory device for storing a clinical protocol definition file comprising the identification data representative of the at least one physical ailment for each of a plurality of human body parts.

4. A reconfigurable physical therapy apparatus as defined in claim 1, wherein said physical therapy applicator means comprises an ultrasound applicator for providing predetermined ultrasonic stimuli to the patient based upon the selected physical ailment.

5. A reconfigurable physical therapy apparatus as defined in claim 4, wherein the predetermined ultrasonic stimuli are defined by a clinical protocol having the predetermined set of transducer operational parameters, the predetermined set of transducer operational parameters being selected from the group consisting of waveform type, number of channels, frequency, duty cycle and treatment time, and wherein said ailment storage means comprises a memory device for storing a clinical protocol definition file comprising the identification data representative of the at least one physical ailment for each of a plurality of human body parts.

6. A reconfigurable physical therapy apparatus as defined in claim 1, wherein said physical therapy applicator provides a plurality of types of predetermined stimuli including electrical stimulation and ultrasonic stimulation, and wherein said physical therapy apparatus further comprises means operatively connected in electrical communication with said ailment storage means for forming an identification data subset from the identification data representative of at least one physical ailment for each of a plurality of human body parts based upon a preselected type of predetermined stimuli such that each set of transducer operational parameters of the identification data subset defines a predetermined transducer operational output which includes the preselected type of predetermined stimuli, and wherein the identification data representative of the at least one displayed physical ailment associated with a human body part which is displayed is selected from the identification data subset.

7. A reconfigurable physical therapy apparatus as defined in claim 1, wherein said ailment storage means comprises a memory device for storing the identification data representative of the at least one physical ailment for each of a plurality of human body parts and the set of transducer operational parameters, and wherein the identification data representative of the at least one physical ailment includes a clinical protocol definition file comprising data representative of the transducer operational parameters which define each respective clinical protocol, and a screen display data file comprising data representative of the displayed information regarding each respective clinical protocol including data representative of the physical ailment associated with each respective clinical protocol.

8. A reconfigurable physical therapy apparatus as defined in claim 7, wherein said physical therapy applicator provides a plurality of types of predetermined stimuli including ultrasonic stimulation and a plurality of types of electrical stimulation for pain management, muscle contraction, and wound healing, and wherein the clinical protocol definition data file includes an ultrasound data subfile, a pain management data subfile, a muscle contraction data subfile, and a wound healing data subfile comprising data representative of the transducer operational parameters which define respective clinical protocols adapted to respectively provide ultrasound therapy, pain management, muscle contraction, and wound healing.

9. A reconfigurable physical therapy apparatus as defined in claim 1, wherein the interactive ailment-protocol selection interface further comprises modification means for modifying at least one parameter of the set of transducer operational parameters corresponding to the selected physical ailment to thereby provide a modified transducer output as defined by the modified parameters.

10. A reconfigurable physical therapy apparatus as defined in claim 9, further comprising selected protocol storage means for storing data representative of the selected physical ailment as modified by said modification means such that the operator of the physical therapy apparatus can retrieve data representative of the previously selected physical ailments from said selected treatment storage means.

11. A reconfigurable physical therapy apparatus as defined in claim 1, further comprising ailment storage means responsive to said ailment selection means for storing data representative of the selected ailment such that the operator of the physical therapy apparatus selectively retrieves data representative of a previously selected ailment protocol from said selected ailment treatment storage means.

12. An interactive ailment-protocol selection interface for responsively configuring an associated physical therapy apparatus, the interactive ailment-protocol selection interface comprising:

ailment storage means for storing identification data representative of at least one predetermined physical ailment for each of a plurality of predetermined human body parts and a corresponding set of predetermined transducer operational parameters associated with each predetermined physical ailment and each predetermined body part so as to define a respective clinical protocol;

a screen display responsive to said ailment storage means for displaying identification data representative of at least one physical ailment for at least one of the predetermined human body parts; and ailment selecting means, operatively connected in electrical communication with said ailment storage means and responsive to operator selection of one of the physical ailments for which representative identification data is displayed, for obtaining the set of predetermined transducer operational parameters associated with the selected physical ailments such that the associated physical therapy apparatus is automatically reconfigured based upon the set of transducer operational parameters obtained by said ailment selecting means to provide therapeutic treatment to the identified body part according to the set of transducer operational parameters.

13. An interactive ailment-protocol selection interface as defined in claim 12, further comprising means operatively connected in electrical communication with said ailment storage means for forming an identification data subset from the identification data representative of at least one physical ailment for each of a plurality of human body parts based upon a preselected type of predetermined stimuli such that each set of transducer operational parameters of the identification data subset defines a predetermined transducer operational output which includes the preselected type of predetermined stimuli, and wherein the identification data representative of the at least one displayed physical ailment associated with a human body part is selected from the identification data subset.

14. An interactive ailment-protocol selection interface as defined in claim 13, wherein said ailment storage means comprises a memory device for storing the identification data representative of the at least one physical ailment for each of a plurality of human body parts and the set of transducer operational parameters, and wherein the identification data representative of the at least one physical ailment includes a clinical protocol definition file comprising data representative of the transducer operational parameters which define each respective clinical protocol, and a screen display data file comprising data representative of the displayed information regarding each respective clinical protocol including data representative of the physical ailment associated with each respective clinical protocol.

15. An interactive ailment-protocol selection interface as defined in claim 14, wherein said physical therapy applicator provides a plurality of types of predetermined stimuli including ultrasonic stimulation and a plurality of types of electrical stimulation for pain management, muscle contraction, and wound healing, and wherein the clinical protocol definition file includes an ultrasound subfile, a pain management subfile, a muscle contraction subfile, and a wound healing subfile comprising data representative of the transducer operational parameters which define respective clinical protocols adapted to respectively provide ultrasound therapy, pain management, muscle contraction, and wound healing.

16. An interactive ailment-protocol selection interface as defined in 12, wherein the interactive ailment-protocol selection interface further comprises modification means for modifying at least one parameter of the set of transducer operational parameters corresponding to the selected physical ailment to thereby provide a modified output as defined by the modified parameters.

17. An interactive ailment-protocol selection interface as defined in claim 16, further comprising selected treatment storage means for storing data representative of the selected physical ailment as modified by said modification means such that the operator of the physical therapy apparatus can retrieve data representative of the previously selected physical ailments from said selected treatment storage means.

18. An interactive ailment-protocol selection interface as defined in claim 12, further comprising ailment storage means responsive to said ailment selection means for storing data representative of the selected ailment such that the operator of the physical therapy apparatus selectively retrieves data representative of a previously selected ailment protocol from said selected ailment protocol storage means, said ailment storage means comprises a memory device for storing the identification data representative of at least one physical ailment for each of a plurality of human body parts and the set of transducer operational parameters, wherein the identification data representative of at least one physical ailment includes a clinical protocol definition file comprising data representative of the transducer operational parameters which define each respective clinical protocol, and a screen display data file comprising data representative of the displayed information regarding each respective clinical protocol including data representative of the physical ailment associated with each respective clinical protocol.

19. A method of responsively configuring a physical therapy apparatus including a transducer, the method comprising:

displaying identification data representative of at least one predetermined physical ailment for at least one predetermined human body part and a corresponding set of predetermined transducer operational parameters for the physical therapy apparatus associated with each predetermined physical ailment for each predetermined body part so as to define a respective clinical protocol;

selecting a displayed physical ailment having a corresponding set of transducer operational parameters for the physical therapy apparatus which defines the predetermined output of the transducer of the physical therapy apparatus; and automatically reconfiguring the transducer operational parameters for the physical therapy apparatus based upon the set of transducer operational parameters corresponding to the selected physical ailment such that the physical therapy apparatus is configured to thereby treat the selected physical ailment.

20. A method as defined in claim 19, further comprising:

providing identification data representative of at least one physical ailment for each of a plurality of human body parts and a corresponding set of transducer operational parameters associated with each predetermined physical ailment and each predetermined body part so as to define a respective clinical protocol, wherein the set of transducer operational parameters defines a predetermined output of the transducer of the physical therapy apparatus for treating the respective physical ailment associated with the clinical protocol.

21. A method as defined in claim 20, wherein the predetermined output of the transducer defined by each clinical protocol is further defined by a plurality of parameters, and wherein said providing step comprises the steps of:

providing a clinical protocol definition file comprising data representative of the transducer operational parameters which define each respective clinical protocol; and providing a screen display data file comprising data representative of the displayed information regarding each respective clinical protocol including identification data representative of the physical ailment associated with each respective clinical protocol.

22. A method as defined in claim 21, wherein the physical therapy apparatus provides a plurality of types of outputs including ultrasonic stimulation and a plurality of types of electrical stimulation for pain management, muscle contraction and wound healing, and wherein said step of providing the clinical protocol definition file comprises the step of providing an ultrasound data subfile, a pain management data subfile, a muscle contraction subfile and a wound healing data subfile comprising data representative of the parameters which define the respective clinical protocols adapted to respectively provide ultrasound therapy, pain management, muscle contraction and wound healing, respectively.

23. A method as defined in claim 20, wherein the predetermined output of the transducer defined by each clinical protocol is further defined by a plurality of predetermined parameters, and wherein the method further comprises the step of modifying at least one parameter of the predetermined output of the transducer defined by the selected clinical protocol to thereby provide a modified output as defined by the modified parameters.

24. A method as defined in claim 23, further comprising the steps of:

storing data representative of the selected clinical protocol as modified in a selected protocol data file; and retrieving the data representative of the previously selected protocol, as modified, from the selected protocol data file.

25. A method as defined in claim 20, further comprising the steps of:

storing data representative of the selected clinical protocol in a selected protocol data file; and retrieving the data representative of a previously selected protocol from the selected protocol data file.

26. A method as defined in claim 20, further comprising the step of forming a subset from the data representative of the plurality of predetermined clinical protocols based upon a predetermined criteria such that each clinical protocol in the clinical protocol subset has the predetermined criteria, and wherein said displaying step comprises the step of displaying data representative of at least one clinical protocol selected from the clinical protocol subset.

27. A method as defined in claim 26, wherein the predetermined criteria is at least one physical ailment such that each clinical protocol in the clinical protocol subset is associated with at least the one physical ailment, and wherein the method further comprises the step of selecting the at least one physical ailment which defines the resulting clinical protocol subset.

28. A method as defined in claim 20, wherein said displaying step comprises the step of displaying data representative of additional clinical protocols including data representative of the respective physical ailments associated with the additionally displayed clinical protocols.

29. A method as defined in claim 20, wherein the predetermined output of the transducer defined by each clinical protocol is further defined by a plurality of predetermined parameters, and wherein the method further comprises the step of displaying data representative of the predetermined parameters defining the transducer output by the selected clinical protocol prior to providing the transducer output.

30. A method of providing operator-selected stimuli from a transducer of a physical therapy apparatus to a patient, the method comprising the steps of:

generating identification data representative of a plurality of predetermined physical ailments for each of a plurality of predetermined body parts and a corresponding set of predetermined transducer operational parameters associated with each predetermined physical ailment and each predetermined body part so as to define a clinical protocol, wherein the set of transducer operational parameters defines a predetermined output of the transducer of the physical therapy apparatus for treating the respective physical ailment associated with the clinical protocol;

displaying identification data representative of at least one of the predetermined physical ailments;

selecting a displayed physical ailment;

automatically reconfiguring the transducer operational parameters of the physical therapy apparatus based upon the clinical protocol associated with the selected physical ailment; and providing a predetermined stimuli from the transducer to the patient based upon the predetermined transducer output defined by the selected clinical protocol to thereby treat the respective physical ailment associated with the selected clinical protocol.

31. A method as defined in claim 30, wherein said step of providing stimuli comprises the step of providing predetermined electrical stimuli from the transducer to the patient based upon the selected clinical protocol, wherein the predetermined electrical stimuli defined by each respective clinical protocol is further defined by data representative of a plurality of transducer operational parameters, the plurality of transducer operational parameters being selected from the group consisting of waveform type, number of channels, frequency, duty cycle, cycle time, amplitude modulation and treatment time, and wherein said generating step comprises the steps of:

generating a clinical protocol definition file comprising identification data representative of the transducer operational parameters which define each respective clinical protocol; and generating a screen display data file comprising data representative of the displayed information regarding each respective clinical protocol including identification data representative of the physical ailment associated with each respective clinical protocol.

32. A method as defined in claim 30, wherein said step of providing stimuli comprises the step of providing predetermined ultrasonic stimuli from the transducer to the patient based upon the selected clinical protocol, wherein the predetermined ultrasonic stimuli defined by each respective clinical protocol is further defined by a plurality of transducer operational parameters, the plurality of transducer operational parameters being selected from the group consisting of frequency, number of channels, duty cycle and treatment time, and wherein said generating step comprises the steps of:

generating a clinical protocol definition file comprising identification data representative of the transducer operational parameters which define each respective clinical protocol; and generating a screen display data file comprising identification data representative of the displayed information regarding each respective clinical protocol including identification data representative of the physical ailment associated with each respective clinical protocol.

33. A method as defined in claim 30, further comprising the step of selecting the type of predetermined stimuli to be provided from the transducer, wherein the plurality of types of predetermined stimuli include electrical stimulation and ultrasonic stimulation.

34. A method as defined in claim 33, further comprising the step of forming a subset from the identification data representative of the plurality of physical ailments based upon the selected type of predetermined stimuli such that each physical ailment in the physical ailment subset defines a predetermined transducer output which includes the selected type of predetermined stimuli from the transducer, and wherein said displaying step comprises the step of displaying identification data representative of at least one physical ailment selected from the physical ailment subset.

35. A method as defined in claim 30, wherein the predetermined transducer output defined by each clinical protocol is further defined by a plurality of predetermined transducer operational parameters, and wherein the method further comprises the step of modifying at least one transducer operation parameter of the predetermined transducer output defined by the selected physical ailment prior to providing the predetermined stimuli such that a modified output, as defined by the modified parameters, is provided.

36. A method as defined in claim 35, further comprising the steps of:

storing data representative of the selected physical ailment as modified in a selected protocol data file; and retrieving the modified data representative of the previously selected physical ailment from the selected protocol data file.

37. A method as defined in claim 30, further comprising the steps of:

storing data representative of the selected physical ailment in a selected protocol data file; and retrieving the data representative of a previously selected physical ailment from the selected protocol data file.

* * * * *